Figure 1:
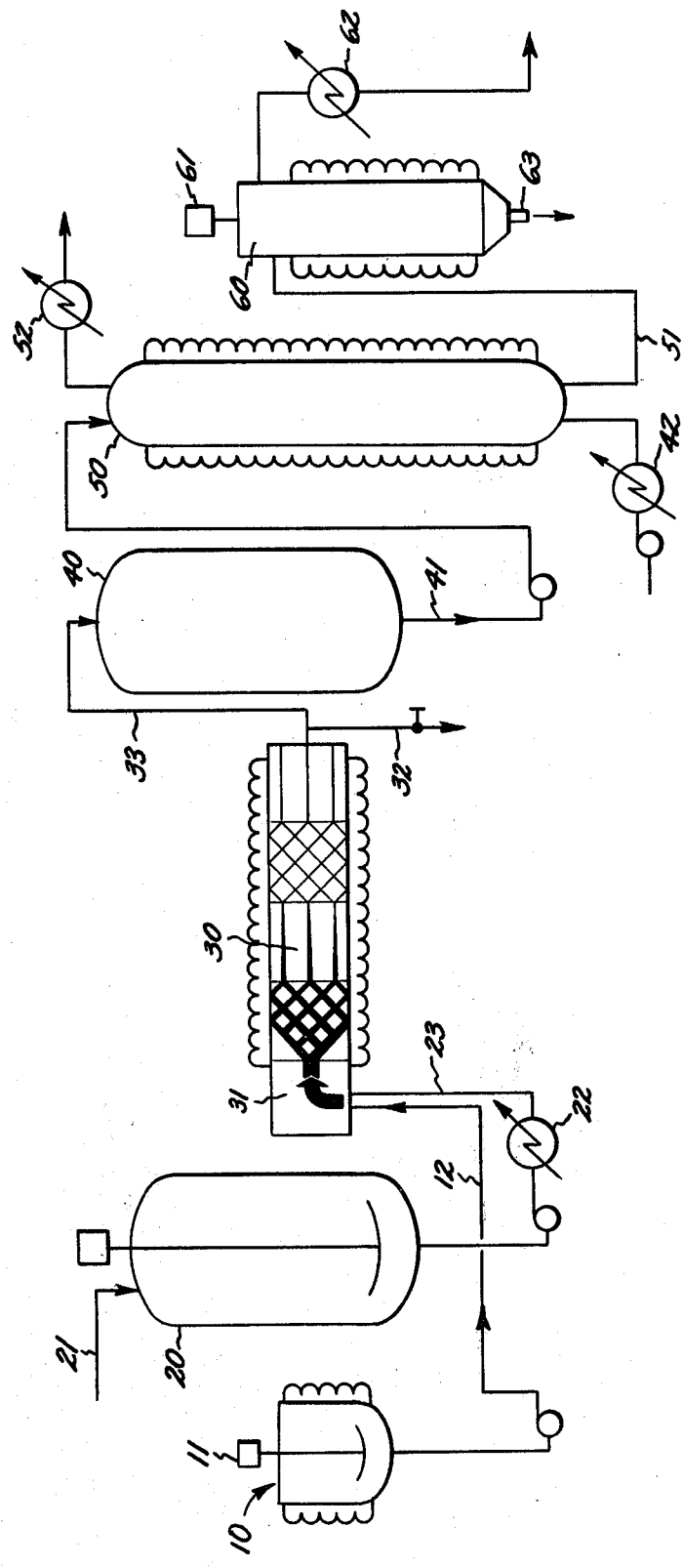

United States Patent [19]

Webb et al.

[11] 4,340,545
[45] * Jul. 20, 1982

[54] METHOD FOR MAKING AROMATIC BIS(ETHER ANHYDRIDES)

[75] Inventors: Jimmy L. Webb, Ballston Lake, N.Y.; Bharat M. Mehta, Pittsfield, Mass.

[73] Assignee: General Electric Company, Schenectady, N.Y.

[*] Notice: The portion of the term of this patent subsequent to May 11, 1999, has been disclaimed.

[21] Appl. No.: 253,446

[22] Filed: Apr. 13, 1981

[51] Int. Cl.$^3$ ............................................. C07D 307/89
[52] U.S. Cl. ...................................................... 549/241
[58] Field of Search ...................................... 260/346.3

[56] References Cited

U.S. PATENT DOCUMENTS 4,116,980  9/1978  Webb ............................... 260/346.3
4,128,574  12/1978  Markezich et al. ................. 562/473

OTHER PUBLICATIONS

Weissberger, Technique of Organic Chem., vol. III, Part I: Separation Purification; Interscience Publishers, (1956), pp. 149–157, 164 and 313.

Primary Examiner—Henry R. Jiles
Assistant Examiner—Bernard Dentz
Attorney, Agent, or Firm—William A. Teoli; James C. Davis, Jr.

[57] ABSTRACT

A method is provided for making aromatic bis(ether phthalic anhydride)s by effecting an imide-anhydride exchange between aromatic bis(ether N-organophthalimide) and phthalic anhydride in the presence of an imide anhydride exchange catalyst and water and extracting the aqueous imide-anhydride exchange reaction mixture with an inert organic solvent. Imide-anhydride exchange product having at least 97 mole percent aromatic bis(ether phthalic anhydride) can be made at substantially reduced temperatures and pressures, by increasing by a factor of at least two, the number of times the imide-anhydride exchange mixture is extracted.

4 Claims, 1 Drawing Figure

METHOD FOR MAKING AROMATIC BIS(ETHER ANHYDRIDES)

CROSS REFERENCE TO RELATED APPLICATIONS

Reference is made to copending application Ser. No. 251,019 filed Apr. 3, 1981 of Jimmy L. Webb and Donald L. Phipps, Jr., for Method for Making Aromatic Bis(Ether Anhydrides) and our copending application Ser. No. 250,804, filed Apr. 3, 1981, for Method for Making Aromatic Bis(Ether Anhydrides), assigned to the same assignee as the present invention.

BACKGROUND OF THE INVENTION

As shown in our copending application Ser. No. 250,804, aromatic bis(ether phthalic anhydride) of the formula,

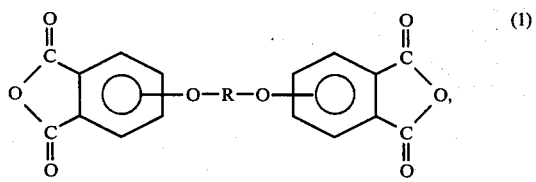

can be made by effecting reaction between an aqueous mixture of phthalic acid and a triorganoamine imide-anhydride exchange catalyst with molten aromatic bis(ether phthalimide) of the formula,

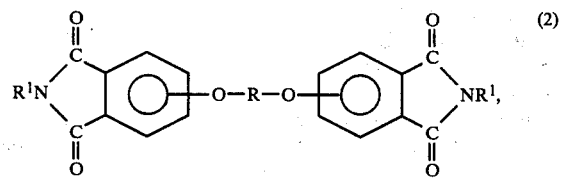

followed by the extraction of the resulting imide-anhydride exchange mixture with an inert organic solvent, where R is a $C_{(6-30)}$ divalent aromatic organic radical, where $R^1$ is a monovalent organo radical selected from the class consisting of $C_{(1-8)}$ alkyl radicals, and $C_{(6-13)}$ aromatic radicals.

It is further taught in Ser. No. 250,804 that the extraction of the imide-anhydride exchange mixture is effected at a temperature of about 200° C. and a pressure of about 500 psi. In order to ensure the recovery of an exchange product having at least 97 mole percent of aromatic bis(ether phthalic anhydride), it has been found that the imide-anhydride exchange mixture has to be extracted at least three times with organic solvent. As a result, high pressure equipment had to be utilized when operating at temperatures of about 200° C., particularly where the organic solvent was a volatile material, such as toluene. As a result, the overall process for making the aromatic bis(ether phthalic anhydride) of formula (1) using the method of Ser. No. 250,804 had to be carefully monitored to satisfy safety regulations.

The present invention is based on the discovery that aromatic bis(ether phthalic anhydride) of formula (1) can be made from molten aromatic bis(ether-N-organophthalimide) of formula (2) in accordance with the aforementioned imide-anhydride exchange reaction, where imide-anhydride exchange product can be recovered having at least 97 mole percent of aromatic bis(ether phthalic anhydride) by increasing the number of times the imide-anhydride exchange mixture is extracted with the inert organic solvent. For example, if the extraction of an imide-anhydride exchange mixture, which has reached steady-state requires three extractions at 200° C. and 500 psi, an equivalent level of extraction efficiency can be obtained using six passes at about 130°–140° C.

STATEMENT OF THE INVENTION

In the process of making aromatic bis(ether phthalic anhydride)s of formula (1) comprising, effecting an exchange reaction between molten aromatic bis(ether phthalimide) and phthalic anhydride in the presence of water and an imide-anhydride exchange catalyst, and thereafter extracting the resulting aromatic bis(ether phthalic anhydride) from the exchange reaction mixture with an inert organic solvent at temperatures of at least 180°–210° C. and pressures up to 500 psi to provide an imide-anhydride exchange product having at least 97 mole percent of aromatic bis(ether phthalic anhydride) whereby high pressure extraction equipment is required to satisfy safety requirements, the improvement which comprises, increasing by a factor of at least 2, the number of times extraction of the imide-anhydride exchange mixture is effected with the inert organic solvent, whereby the imide-anhydride exchange product having at least 97 mole percent of aromatic bis(ether phthalic anhydride) can be recovered at temperatures of about 120° C. to 160° C. and pressures of 125–160 psi, whereby the need for high pressure equipment to satisfy safety requirements is substantially avoided.

Radicals included by R are more particularly

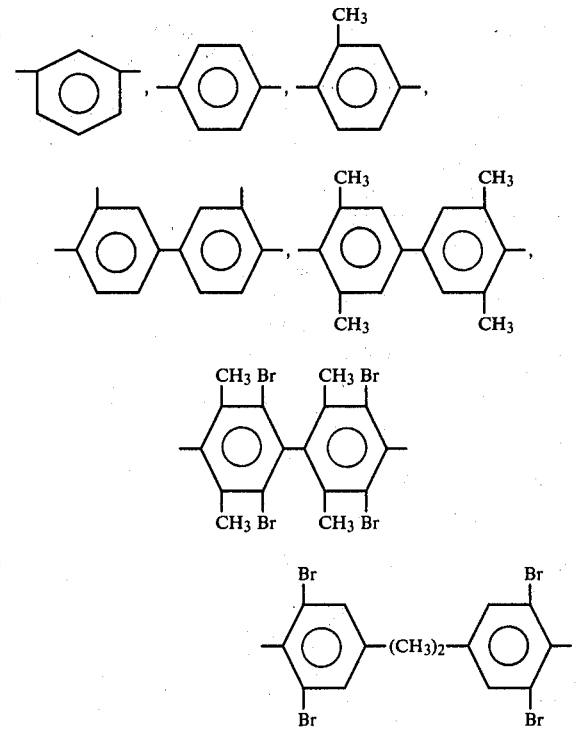

and divalent organic radicals of the general formula,

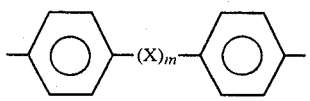

where X is a member selected from the class consisting of divalent radicals of the formulas,

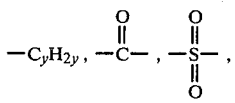

—O—, and —S—, where m is 0 or 1, and y is a whole number from 1 to 5.

Radicals included by $R^1$ are, for example, phenyl, tolyl, xylyl, naphthyl, chlorophenyl, bromonaphthyl, etc., and alkyl radicals, such as methyl, ethyl, etc.

As further shown in U.S. Pat. No. 3,879,428, the aromatic bis(ether phthalimide)s of formula (2) can be made by effecting reaction between phthalimides of the formula,

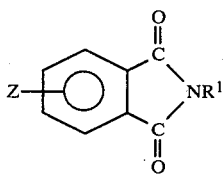

where Z is a radical selected from the class consisting of nitro, halo, fluoro, bromo, etc., and $R^1$ is as previously defined, and alkali diphenoxide of the formula,

where R is as previously defined, and M is a metal ion of an alkalide metal selected from the class consisting of sodium, potassium, lithium, etc.

Included by the alkali diphenoxides of formula (4), are sodium and potassium salts of the following dihydric phenols,
2,2-bis(2-hydroxyphenyl)propane;
2,4′-dihydroxydiphenylmethane;
bis-(2-hydroxyphenyl)methane;
2,2-bis-(4-hydroxyphenyl)propane hereinafter identified as "Bisphenol-A" or "BPA";
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4′-dihydroxybiphenyl;
4,4′-dihydroxy-3,3,5,5′-tetramethylbiphenyl;
2,4′-dihydroxybenzophenone;
4,4′-dihydroxydiphenylsulfone;
2,4′-dihydroxydiphenylsulfone;
4,4′-dihydroxydiphenyl sulfoxide;
4,4′-dihydroxydiphenyl sulfoxide;
4,4′-dihydroxydiphenyl sulfide;
hydroquinone;
resorcinol;
3,4′-dihydroxydiphenylmethane;
3,4′-dihydroxybenzophenone;
4,4′-dihydroxybenzophenone; and
4,4′-dihydroxydiphenylether.

A more complete understanding of the practice of the method of the present invention can be obtained by reference to the drawing.

There is shown an aromatic bis(ether imide), or "bisimide" melt tank and a tank for an aqueous mixture of phthalic acid and imide-anhydride exchange catalyst which is fed into a horizontal reactor. The resulting imide-anhydride exchange reaction mixture is conveyed to a holding tank and then into an extraction column. The resulting aqueous mixture is fed into a vertical thin film evaporator resulting in the separation of aromatic bis(ether anhydride), or "bisanhydride" from the bottom of the evaporator and recovery of an aqueous mixture of phthalic acid and imide-anhydride exchange catalyst such as trimethylamine, triethylamine, tripropylamine, from the top of the vertical thin film evaporator.

More particularly there is shown at 10 a bisimide melt tank with an agitator 11 and a heated feed line at 12 which conveys the molten bisimide to reactor 30. Simultaneously, an aqueous mixture of phthalic acid and imide-anhydride exchange catalyst is fed via line 21 into tank 20 which thereafter is passed through a heat exchanger 22 before it is conveyed through a heated line to reactor 30. Thorough mixing of the molten bisimide and the aqueous phthalic anhydride feed, which are maintained at flow rates sufficient to maintain a ratio of 6 moles of phthalic acid per mole of bisimide, is achieved by passing the feed streams through a mixing zone at 31 prior to entering reactor 30. The heat exchanger 22 is operated to advance the temperature of the phthalic acid mixture to 200° C. After a residence time of about 10 minutes or less in the reactor at temperatures of 200° C. to 220° C., and pressure of 300 psi to 500 psi, the mixture is then fed through a heated line 33 into holding tank 40. A valve 32 provides a means for sampling the mixture from reactor 30. The imide-anhydride exchange mixture is then fed through a heated line 41 into an extraction column 50 at a temperature in the range of about 120°–150° C. Extraction solvent is fed into the extraction column after passing through a heat exchanger 42 to bring the solvent up to a temperature of approximately 120° C. to 150° C. Suitable extraction solvents are, for example, toluene, benzene, o-dichlorobenzene, chlorobenzene, etc. An organic solvent solution of the imide-anhydride extraction, for example, N-organophthalimide, bisimide, etc., is passed through a heat exchanger at 52 and recovered for recycling.

The aqueous exchange mixture is extracted at least 6 times more or less depending upon the desired degree of removal of the N-organophthalimide containing materials from the aromatic bis(ether phthalic anhydride). The bis(ether anhydride) is recovered from the vertical thin film evaporator 60 at orifice 63. Depending upon the number of theoretical plates used in the extraction column, the actual number of passes through the column can vary. It has been found, for example, that if the extraction column is operated at a temperature in the range of about 200° C. only 1 pass through a column of 3 theoretical plates is required. Accordingly, twice as many passes or theoretical plates are required at a temperature of 135° C. than that required for 200° C.

An aqueous exchange mixture is separated at the bottom of the extraction column 50 and fed into a vertical thin film evaporator 60 through line 51. Rotating wiper blades at 61 in evaporator 60 facilitate the evaporation of an aqueous mixture of phthalic acid and imide-anhydride exchange catalysts which is condensed in heat exchanger 62. The desired bisanhydride in a molten state is recovered at 63.

Preferably the imide-anhydride exchange catalyst is a trialkylamine, for example, triethylamine, tributylamine, etc., while triethylamine is particularly preferred.

In order that those skilled in the art will be better able to practice the present invention, the following examples are given by way of illustration and not by way of limitation. All parts are by weight.

EXAMPLE 1

A mixture of 41 parts of 2,2-bis[4-(3,4-dicarboxyphenoxy)phenyl]propane bis-N-methylimide, 67 parts of phthalic anhydride, 91 parts of triethylamine and 75 parts of water was heated in a autoclave, which had been flushed with nitrogen, to 200° C. for 0.5 hour. The autoclave was then cooled to 130° C. and 415 parts of toluene was pumped into the aqueous mixture. The toluene and aqueous mixture were held at 130° C. and 65 psi for 0.25 hour with stirring. The mixture was then allowed to cool to 25° C. and separation between the organic layer and the aqueous layer was effected. The aqueous layer was then reheated under sealed conditions after it had been flushed with nitrogen and the extraction with toluene was repeated. This procedure was duplicated seven times. Each time, a portion of the aqueous layer was retained for analysis. The results obtained from the aforementioned procedure are shown in the following table, where composition is given in mole percent. "Composition Mole Percent" shows the mole percent of the ingredients in the aqueous phase, where "BI" is aromatic bis(ether phthalimide), "IA" is the corresponding imide-anhydride and "DA" is aromatic bis(ether phthalic anhydride).

TABLE I

| Composition of Imide-anhydride Exchange Product (Mole %) | | | |
| --- | --- | --- | --- |
| Extraction | BI | IA | DA |
| 0 | 7.05 | 32.64 | 60.31 |
| 1 | 0.30 | 29.10 | 70.60 |
| 2 | 0.03 | 16.47 | 83.5 |
| 3 | 0.03 | 8.14 | 91.83 |
| 4 | 0.02 | 5.04 | 94.93 |
| 5 | 0.02 | 3.66 | 96.31 |
| 6 | 0.02 | 2.13 | 97.85 |

The above results show that low temperature extraction at about 130° C. is capable of providing an imide-anhydride exchange product having at least 97 mole percent of aromatic bis(ether phthalic anhydride) after 6 extractions at a temperature of about 130° C. and a pressure of 60 psi.

EXAMPLE 2

In accordance with the drawing, an imide-anhydride exchange was conducted in a reactor filled with Koch Static Mixers of the Koch Engineering Company, New York, N. Y. at a temperature of about 200° C. and a 300 psi pressure. Molten 2,2-bis[4-(3,4-dicarboxyphenoxy)-phenyl]propane, bis-N-methylimide was heated in a melt tank to about 180° C. and fed into the reactor with an aqueous mixture of phthalic acid and triethylamine, utilizing a proportion of 2 moles of triethylamine per mole of phthalic acid, which was employed at about 28% by weight in the aqueous mixture based on the weight of phthalic acid, water and amine. After the imide-anhydride reaction mixture had achieved equilibrium, the mixture was allowed to cool to 140° C. and then extracted with toluene at about 140° C. in the column shown in the drawing. The imide-anhydride mixture at equilibrium was extracted with toluene and the mole % of 2,2-bis[4-(3,4-dicarboxyphenoxy)-phenyl]propane dianhydride, "bisanhydride" remaining in the mixture was measured after each pass. The following resulting were obtained, where BI, IA, and DA are as previously defined:

TABLE II

| Column Pass | Sum of Stages | Aqueous Phase Composition mole % | | |
| --- | --- | --- | --- | --- |
| | | % BI | % IA | % DA |
| 1 | 3 | 0.03 | 11.2 | 88.8 |
| 2 | 6 | 0.02 | 5.4 | 94.6 |
| 3 | 9 | 0.01 | 3.0 | 97 |

The above results show that extraction of an imide-anhydride exchange mixture at equilibrium can be achieved with toluene at a temperature of about 140° C. and a pressure of about 150 psi to obtain an exchange product having at least 97 mole % bisanhydride.

Although the above examples are directed to only a few of the very many variables which can be used in the practice of the present invention, it should be understood that the present invention is directed to the use of a much broader variety of aromatic bis(ether phthalimides) which can be converted to aromatic bis(ether phthalic anhydride) by the use of phthalic acid, water and various imide-anhydride exchange catalysts.

What we claim as new and desire to secure by Letters Patent of the United States is:

1. In the process of making aromatic bis(ether phthalic anhydride)s of the formula,

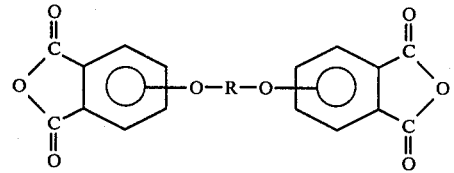

comprising effecting an exchange reaction between molten aromatic bis(ether phthalimide) and phthalic anhydride in the presence of water and an imide-anhydride exchange catalyst, and thereafter extracting the resulting mixture from the exchange reaction mixture with an inert organic solvent to produce an imide-anhydride exchange product having at least 97 mole % of the aromatic bisanhydride requiring temperatures of about 200° C. and pressures up to 500 psi whereby high pressure extraction equipment is required creating hazardous extraction conditions, the improvement which comprises increasing by a factor of at least 2, the number of times extraction of the imide anhydride exchange mixture is effected with the inert organic solvent, whereby the exchange product having at least 97 mole % of bisanhydride can be recovered at temperatures of about 160° C. or less and the need for high pressure equipment and hazardous extraction conditions is substantially avoided where R is a $C_{(6-30)}$ divalent organic radical.

2. A process in accordance with claim 1, where the aromatic bis(ether phthalimide) is 2,2-bis[4-(3,4-dicarboxyphenoxy)phenyl]propane bis-N-methylimide.

3. A process in accordance with claim 1, where the aromatic bis(ether phthalic anhydride) is 2,2-bis[4-(3,4-dicarboxyphenoxy)phenyl]propane dianhydride.

4. A process in accordance with claim 1, where the imide anhydride exchange catalyst is triethylamine.

* * * * *